(12) United States Patent
Steimer et al.

(10) Patent No.: US 7,005,263 B1
(45) Date of Patent: Feb. 28, 2006

(54) TRANSCRIPTIONALLY SILENCED PLANT GENES

(75) Inventors: Andrea Steimer, Zurich (CH); Ortrun Mittelsten Scheid, Basel (CH); Jerzy Paszkowski, Nenzlingen (CH)

(73) Assignee: Syngenta Participations AG, Basel (CH)

( * ) Notice: Subject to any disclaimer, the term of this patent is extended or adjusted under 35 U.S.C. 154(b) by 245 days.

(21) Appl. No.: 10/088,384

(22) PCT Filed: Sep. 14, 2000

(86) PCT No.: PCT/EP00/08994

§ 371 (c)(1),
(2), (4) Date: Mar. 15, 2002

(87) PCT Pub. No.: WO01/20010

PCT Pub. Date: Mar. 22, 2001

(30) Foreign Application Priority Data

Sep. 16, 1999 (GB) .................................. 9921964

(51) Int. Cl.
*C12Q 1/68* (2006.01)
*C07H 21/04* (2006.01)

(52) U.S. Cl. .......................................... 435/6; 536/23.6
(58) Field of Classification Search ............... 536/23.6; 435/6
See application file for complete search history.

(56) References Cited

OTHER PUBLICATIONS

Ausubel et al., Short Protocols In Molecular Biology, 3rd Ed., 1997, John Wiley & Sons, Inc., New York, NY, pp. 14-16 to 14-19.*
Dante E., "F7N22.8 Protein" Database SWALL [online] EMBL; AC/ID AC065225 (Aug. 1, 1998).
Dante et al., "The sequence of *A. thaliana* F7N22" Database EM_PL [online] EMBL; AC/ID AF058825 (Apr. 16, 1998).
Jordan et al., "*Arabidopsis thaliana* DNA chromosome 3, BAC clone T15B3" Database EM_PL [online] EMBL; AC/ID AL163975 (Apr. 17, 2000).
Kotani H. and Kumekawa N., "*Arabidopsis thaliana* DNA, chromosome 5 centromere region, clone:F26M13" Database EMBLNEW [online] EMBL; AC/ID AB046429 (Sep. 5. 2000).
Kumekawa et al., *The Size and Sequence Organization of the Centromeric Region of Arabidopsis Thaliana Chromosome 5* DNA Research, vol. 7 (2000), pp. 315-321.
Lin et al., "*Arabidopsis thaliana* 'TAMU' BAC 'T6C20' genomic sequence near marker 'g4532'" Datababe EM_HTG [online] EMBL; AC/ID AC005898 (Nov. 2, 1998).
Lin et al., "*Arabidopsis thaliana* chromosome II section 74 of 255 of the complete sequence. Sequence from clones F15011, F1404, T26C18." Database EM_PL [online] EMBL; AC/ID AC007209 (Apr. 4, 1999).
Liu et al., "*Arabidopsis thaliana* chromosome 1 BAC F9D18 sequence" Database EM_HTG [online] EMBL; AC/ID AC007183 (Mar. 3, 1999).
Mittelstein Scheid et al., *Release of epigenetic gene silencing by trans-acting mutations in Arabidopsis* Proceedings of the National Academy of Science, USA, vol. 95 (Jan. 1998) pp. 632-637.
Paszkowski et al., *Plant Genes: The Genetics of Epigemetics* Current Biology, vol. 8, (1998) R206-R208.
Steimer et al., *Endogeneous Targets of Transcriptional Gene Silencing in Arabidopsis* The Plant Cell, vol. 12 (Jul. 2000) pp. 1165-1178.
Strowmatt et al., "The Sequence of *A. thaliana* T9E19" Database EM_PL [online] EMBL; AF/ID AF104920 (Nov. 11, 1998).

* cited by examiner

*Primary Examiner*—Ashwin Mehta
(74) *Attorney, Agent, or Firm*—Mary Kakefuda

(57) ABSTRACT

The invention relates to gene silencing as observed after integration of transgenes into plant genomes. Comparison of transcriptional gene expression between an *Arabidopsis* line carrying a silent transgene present in multiple copies and its mutant derivative mom1 impaired in silencing of the transgene revealed two cDNA clones which are expressed in the mutant plants, but not in the parental and not in wild type plants. Both clones are derived from the same family of transcripts referred to as TSI (Transcriptionally Silent Information). Genomic templates encoding TSI are repetitive elements with mainly pericentromeric location and conserved organization among various ecotypes. Transcriptional silencing of the genomic TSI templates is specifically released in the mutant. Transcription of TSI can be used as a marker to identify a defective silencing pathway in a plant.

5 Claims, No Drawings

TRANSCRIPTIONALLY SILENCED PLANT GENES

CROSS-REFERENCE TO RELATED APPLICATIONS

This application is a § 371 of International Application No. PCT/EP00/08994, filed Sep. 14, 2000.

BACKGROUND OF INVENTION

The present invention relates to the field of gene expression in plants and in particular concerns gene silencing, a phenomenon frequently observed after integration of transgenes into plant genomes. Comparison of transcriptional gene expression between an *Arabidopsis* line carrying a silent transgene present in multiple copies and its mutant derivative mom1 impaired in silencing of the transgene revealed two cDNA clones which are expressed in the mutant plants, but not in the parental and not in wild type plants. Both clones are derived from the same family of transcripts which we refer to as TSI (Transcriptionally Silent Information). The disclosed genomic templates encoding TSI are repetitive elements with mainly pericentromeric location and conserved organizaton among various ecotypes. They are also referred to as TSI. Transcriptional silencing of the genomic TSI templates is specifically released in the mutant. Silencing of said templates is further released in other genotypes known to affect transcriptional gene silencing. Thus, transcription of TSI can be used as a marker to identify a defective silencing pathway in a plant.

Correct balance between activation and silencing of its genetic information is essential for any living cell. A tight control of gene expression is necessary for adaptation to environmental factors, regulation of physiological requirements, and development of differentiated, specialized cell types within a multicellular organism. For example differentiation processes involve mitotically heritable changes of gene expression, wherein the acquired states of gene activity gain a certain stability. This stability can be achieved by the strict control of gene activators, by regulation of transcript stability, or by regulating the transcriptional availability of genetic information itself as by stable silencing of selected genetic loci. Silencing has been frequently observed in connection with repression of transgene expression in various experimental systems.

In plants, silencing of transgenic loci limits the reliability of transgenic approaches to improve quality traits. It has been noticed that complex inserts containing rearranged multiple copies of a transgene are particularly prone for gene silencing. Two different mechanisms leading to loss of transgene expression are observed. The first prevents transcription (transcriptional gene silencing or TGS), and the second targets selected transcripts for rapid degradation (posttranscriptional gene silencing or PTGS). Triggers of both processes seem to be similar, since the onset of both types of silencing correlates with redundancy of genetic information, i.e. DNA repeats in case of TGS and RNA overproduction for PTGS. TGS is meiotically heritable and correlates with DNA template modification manifested by hypermethylation of promoters of silenced genes or with local changes of chromatin structure. In contrast, PTGS is not meiotically transmitted and needs to be reestablished in each sexual generation. PTGS does not require modification of a DNA template, however, increased levels of DNA methylation within the protein-coding region of silenced genes have been observed.

The majority of silencing studies in plant systems deal with silencing of transgenes. There are only a few examples of gene silencing without involvement of transgenic loci. The criteria for TGS susceptibility of genetic information is very poorly understood, and the natural targets of transcriptional silencing in a normal, wild type plant are yet to be discovered. It has been postulated that TGS is a defense system against invasive DNA such as transposable elements but experimental evidence for this hypothesis is lacking.

DEFINITIONS

Within the context of the present invention reference to a gene is to be understood as reference to a DNA coding sequence associated with regulatory sequences, which allow transcription of the coding sequence into RNA such as mRNA, rRNA, tRNA, snRNA, sense RNA or antisense RNA. Examples of regulatory sequences are promoter sequences, 5' and 3' untranslated sequences, introns, and termination sequences.

A promoter is understood to be a DNA sequence initiating transcription of an associated DNA sequence, and may also include elements that act as regulators of gene expression such as activators, enhancers, or repressors.

Expression of a gene refers to its transcription into RNA or its transcription and subsequent translation into protein within a living cell.

Any part or piece of a specific nucleotide or amino acid sequence is referred to as a component sequence.

SUMMARY OF THE INVENTION

It is the aim of the present invention to provide nucleic acid molecules encoding genetic information which is not expressed, i.e. silenced, in wild type plants but whose expression is turned on in plants which are defective in transcriptional gene silencing. Said molecules can be defined by the formula $R_A$—$R_B$—$R_C$, wherein $R_A$, $R_B$ and $R_C$ indicate component sequences consisting of nucleotide residues independently selected from the group of G, A, T and C or G, A, U and C, wherein G is Guanosinmonophosphate, A is Adenosinemonophosphate, T is Thymidinmonophosphate, U is Uridinmonophosphate and C is Cytidinmonophosphate;

$R_A$ and $R_C$ consist independently of 0 to 6000 nucleotide residues;

$R_B$ consists of at least 50 nucleotide residues; and the component sequence $R_B$ is at least 80% identical to an aligned component sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 27.

In a preferred embodiment of the present invention $R_B$ consists of at least 100 nucleotide residues and is at least 85% identical to an aligned component sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 27.

In another preferred embodiment $R_B$ consists of at least 200 nucleotide residues and is at least 90% identical to an aligned component sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 27.

Specific examples of $R_B$ are the sequences given in SEQ ID NO: 7, SEQ ID NO: 9 and SEQ ID NO: 27.

Additionally, $R_A$ or $R_C$ may comprise one or more component sequences with a length of at least 50 nucleotide residues and at least 90% identical to an aligned component sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 27.

The nucleic acid molecules according to the present invention exist either in the form of DNA or as RNA. Preferred embodiments are genomic DNA, cDNA, plasmid DNA or RNA transcribed therefrom.

DETAILED DESCRIPTION

Nucleotides 437–2383 of SEQ ID NO: 1 encode a putative open reading frame of 648 amino acids (SEQ ID NO: 10) which in SEQ ID NO: 1 is interrupted by a stop codon spanning nucleotides 1631–1633. Nucleic acids encoding a protein comprising a component sequence of at least 200 amino acids length being at least 85% identical to an aligned component sequence of SEQ ID NO: 10 are a further preferred embodiment of the present invention.

The nucleic acids according to the present invention represent an endogenous target of the transcriptional silencing system. Example 1 describes the cloning of specific embodiments of the present invention from Arabidopsis. The preferred size of transcribed RNA is between 1000 and 6000 nucleotides, particularly transcripts of about 1250, 2500, 4700 and 5000 nucleotides, which can be polyadenylated or not. The transcriptionally silent information present in the genome of wild type plants is found to be only expressed in a range of mutants affected in the maintenance of transcriptional silencing. Importantly, not only strains affected in transcriptional silencing through alterations of genome-wide DNA methylation, but also silencing mutants with unchanged methylation levels which do not show striking phenotypic alterations activate TSI, indicating that the release of silencing from endogenous templates does not require loss of methylation.

Initially two independent clones representing RNA which is specifically expressed in silencing mutants have been cloned. Anticipating that in wild type plants there are probably many more DNA templates suppressed by the silencing system, it is remarkable that parts of the two cDNAs cloned are closely related to each other and it is most likely that they are parts of the same transcript. The three main TSI transcripts of 5000, 2500 and 1250 nucleotides all contain a middle element isolated as TSI-A (SEQ ID NO: 5). The 5000 nt and the 2500 nt transcripts additionally enclose the second isolated element TSI-B (SEQ ID NO: 6), which is like TSI-A without protein coding capacity. The 5000 nucleotide long transcript further comprises a 5' extension (SEQ ID NO: 1 which is similar to SEQ ID NO: 2) encoding a putative open reading frame of 648 amino acids (SEQ ID NO: 10). The two 3' extension clones of TSI-A (SEQ ID NO: 3 and SEQ ID NO: 4) contain a region which can be aligned with nucleotides 1–569 of SEQ ID NO: 6 (nucleotides 808–1397 of SEQ ID NO: 3 and nucleotides 819–1365 of SEQ ID NO: 4) closely related to TSI-B (77% identity). Both the 5000 and the 2500 nucleotide transcripts are polyadenylated, while the most abundant transcript of 1250 nucleotides is absent from the polyA fraction of mom1 RNA and might be retained in the nucleus.

All RNA species originate from unidirectional transcription, but it is not clear if they represent separate transcriptional units regulated by different promoters or if they are processing products of the same long transcript. A refined analysis of the TSI expression pattern is complicated by the multiplicity of potential chromosomal templates and their location mainly in the pericentromeric areas. The novel TSI sequences do not reveal any putative function by sequence similarity to protein- or RNA-coding sequences. The only extensive similarity found was to the 3' halt of the putative, degenerated retrotransposon Athila (Pélissier et al. 1995). The other part of Athila directly adjacent to the TSI template region was not reactivated in the silencing mutant. This suggests that epigenetic transcriptional silencing in Arabidopsis is not directed towards retrotransposons in general, although its targets may have originated from transposition events. This is further supported by the lack of transcriptional reactivation of other Arabidopsis retroelements, e.g. the Ta superfamily (Konieczny et al. 1991). Therefore, only specific pericentromeric repeats seem to be under epigenetic control, in the same way that only a subset of transgenic loci is susceptible to silencing. The existence of remnants of transpositions is probably due to their chromosomal location rather than to sequence specificity, since degenerated retroelements have repeatedly been found in centromeric locations in fungi and plants.

One of the features proposed as a prerequisite for centromere function is late replication of the heterochromatic centromeres and pericentromeric areas in Schizosaccharomyces pombe and higher eukaryotes. If this was also true for Arabidopsis centromeres, undue loosening of suppressive chromatin leading to TSI expression could cause disturbances in mitosis, which would result in severe phenotypes. However, the mom mutant plants exhibit no abnormalities suggesting mitotic disorders. Therefore, transcriptional reactivation of some usually silent pericentromeric repeats, such as described here, does not impair their putative function. Alternatively, their silencing may be important under a specific, still undefined condition or on a longer time scale.

Finally, TSI expression is observed in cells growing for a long time in suspension culture. No release of TSI silencing is observed in any tissue of Arabidopsis wild type plants, including freshly initiated callus cultures. This suggests that an escape from the silencing control is not correlated primarily with dedifferentiation but could be the result of prolonged selection for fast growing dedifferentiated cells. Such a loss of silencing control could also underlie the accumulation of somaclonal variation during prolonged culture and resembles the situation in cells of actively proliferating carcinomas.

Nucleic acids according to the present invention are particularly useful in selecting plants which compared to wild type Arabidopsis plants of all available Arabidopsis ecotypes are impaired in transcriptional gene silencing. A method allowing to select such plants comprises a) separately preparing RNA of a series of plants;

b) probing said RNA preparations with a nucleic acid according to the present invention; and c) identifying a plant whose RNA hybridizes with said nucleic acid.

In a preferred embodiment the probing step is performed after size fractionation of the RNA preparation by gel electrophoresis. For detection the probe is either radioactively labeled or labeled by other chemical modifications.

In another preferred embodiment of said method the step of probing consists of hybridizing the RNA with an oligo nucleotide primer, extending said primer by reverse transcription and subsequent PCR amplification of the DNA generated using oligonucleotide primers specific for SEQ ID NO: 1, SEQ ID NO: 5, SEQ ID NO: 7, SEQ ID NO: 8, SEQ ID NO: 9, or SEQ ID NO: 27. Plants which allow for the amplification of DNA fragments flanked by the oligonucleotide primers are identified as plants whose RNA hybridizes to the nucleic acid according to the invention.

Having available nucleotide sequence information of a genomic region, which is not expressed, i.e. transcriptionally silenced, in a wild type plant, allows to produce DNA representing at least part of a gene necessary to maintain silencing of this genomic region. Preferably the complete gene is produced. A corresponding method of production comprises (a) mutagenizing-wild type cells or plants by randomly inserting into their genomes a DNA tag with known sequence;
(b) identifying mutants of said cells or plants which express RNA that is not expressed in wild type cells or plants;
(c) cloning genomic DNA surrounding or close to the insertion site of the DNA tag;
(d) screening a genomic library of wild type cells or plants with the piece of genomic DNA obtained in process step (c) or a part thereof;
(e) identifying clones comprising at least part of the gene affected by the insertion of the DNA tag; and
(f) further processing the clones obtained in step (e) using recombinant DNA techniques.

In plant cells and plants mutagenesis is preferably achieved performing T-DNA insertion mutagenesis (Dilkes and Feldmann, 1998), or transposon tagging using the En/I (Pereira and Aarts, 1998) or the Ac/Ds system (Long and Coupland, 1998) as described in *Arabidopsis* protocols edited by Martinez-Zapater and Salinas, 1998. Other known physical or chemical methods of mutagenesis such as fast neutron irradiation or EMS mutagenesis (Feldmann et al., 1994) might require adaptation of the above method, but can be used for the production of equivalent DNA involved in the maintenance of silencing as well.

A convenient way to identify RNA that is expressed in mutant cells or plants but not in wild type cells or plants is reverse transcription of said RNA and subsequent PCR amplification of the generated DNA using oligonucleotide primers specific for said DNA (RT-PCR). This allows to pool the RNA of upto 1000 mutants which increases the speed of the identification step considerably.

The methods described above can be further elaborated and developed into a kit for the identification of plants impaired in transcriptional gene silencing. Such a kit necessarily comprises a) a nucleic acid according to the present invention conveniently labeled to be used as a hybridization probe or
b) an oligonucleotide primer for reverse transcription of RNA and an oligonucleotide primer specific for a nucleic acid according to the present invention.

The oligonucleotide primer for reverse transcription can be a poly T primer or an oligonucleotide primer specific for a nucleic acid according to the present invention. The primers specific for nucleic acids according to the present invention are designed to allow PCR amplification of DNA templates characterized by the nucleotide sequences disclosed in the present invention.

EXAMPLES

Example 1

Differential mRNA Screening and Cloning of *Arabidopsis* TSI Sequences

Total RNA of the mutant line mom1 (Amedeo et al, 2000) and its parental line A is isolated according to Goodall et al. (1990) using 2 g fresh weight of two-week-old seedlings. Polyadenylated RNA is obtained using Dynabeads Oligo $(dT)_{25}$ (Dynal). 2 $\mu$g of poly(A) RNA is used for suppression subtractive hybridization (SSH, Diatchenko et al, 1996) using the PCR-Select cDNA subtraction kit (Clontech) according to the suppliers' instructions. cDNA derived from the mutant line mom1 is used as tester and cDNA derived from the parental line A as driver cDNA population. The subtracted library is cloned into vector pCR.2.1 (Invitrogen). 500 individual bacterial cultures from this library are grown according to the manual of the PCR-Select differential screening kit (Clontech). To reduce the number of false positive clones, the library is primarily screened by inverted Northern blots as described by von Stein et al. (1997), Twelve among the 500 primarily selected cDNA clones show increased abundance upon hybridization with labeled mom1 cDNA. Direct Northern blot analysis comparing total RNA of the wild type and the mutant line with these 12 cDNAs as probes reveal a striking genotype-dependent differential expression for two of them. Said clones are sequenced using conventional rhodamine or dRhodamine dye terminators from PE Applied Biosystems and a Perkin-Elmer GeneAmp PCR system 2400, 9600 or 9700 thermocycler. The sequence reactions are analyzed using an ABI PRISM 377 DNA sequencer. The cDNA clones are named TSI-A (903 bp, SEQ ID NO: 5) and TSI-B (614 bp, SEQ ID NO: 6). Both are abundant in the mom1 RNA but are undetectable in *Arabidopsis* line A and wild type *Arabidopsis*, No consistent differential expression between mutant and wild type is observed for the remaining 10 cDNAs.

5' and 3' extension reactions are performed using Clontech's Marathon Kit according to the manufacturer's instructions. Sequence specific primers are
TA-F1: 5'-TGGTTCACCAGATAAGCTCAGTGCCCTC-3' (SEQ ID NO: 11) and
TA-F2: 5'-CTTCAGACTGGATAGGACTAGGTGGGCG-3' (SEQ ID NO: 12, nested primer), for the 3' extension reaction and
TA-R1: 5'-CGCCCACCTAGTCCTATCCAGTCTGAAG-3' (SEQ ID NO: 13) and
TA-R2: 5'-CGCATCAAACAACTAACAACGAGGGCAC-3' (SEQ ID NO: 14, nested primer). for the 5' extension.

PCR amplification products are cloned into vector pCR2.1 (Invitrogen). Individual bacterial cultures are grown and subjected to colony PCR as described in the manual of Clontech's PCR-Select Differential Screening Kit, with the primer combinations used to create the extension reactions (Marathon Adapter primer Ap1 (Clonetech) combined with TA-R2 or TA-F2 for the 5'- or 3' extension reactions, respectively). To screen for positive TSI-A extension clones, the PCR products are blotted and hybridized to TSI-A. All PCR reactions for cloning procedures are performed with a polymerase mix performing proofreading activity (Advantage cDNA PCR Kit, Clontech).

Since only two transcripts are detected in the polyadenylated RNA fraction of mom 1 plants, this RNA is used for 5' and 3' extensions reactions starting from the TSI-A sequence. Two clones each are analyzed at the nucleotide sequence level. The 5' extension yields inserts of 2512 bp (clone a, SEQ ID NO: 1) and 1997 bp (clone b, SEQ ID NO: 2), which after alignment are 97% identical to each other. The clones from the 3' extension have a length of 1682 bp (clone c, SEQ ID NO: 3) and 1652 bp (clone d, SEQ ID NO: 4) and are 94% identical. Interestingly, both 3' extension clones of TSI-A contain a region of 569 bp closely related to TSI-B (77% identity). This explains the detection of similar RNA species on Northern blots with TSI-A and TSI-B as probes and their hybridization to the same YAC and BAC clones, and suggests that TSI-A and TSI-B are part of the same polyadenylated transcript species expressed in the mom1 mutant. To confirm that the 5' extensions of TSI-A are indeed part of the TSI transcripts, a mom1 Northern blot is probed with a cDNA fragment close to the 5' end of the extension (probe ORF corresponding to nucleotides 943–1334 of SEQ ID NO: 1). Interestingly, only the about 5000 nt long transcripts in the poly(A) fraction hybridize to this probe. Since this class of transcripts hybridizes to TSI-A and TSI-B, the 5000 nt transcripts are probably produced from templates containing a particular order of all three sequence elements.

Example 2

Northern and Southern Blot Analysis and Library Screens

Total RNA is either isolated as described by Goodall et al. (1990) or by the RNeasy Plant Mini Kit (Qiagen) according to the suppliers' instructions. For Northern blot analysis, the RNA is electrophoretically separated after denaturation by glyoxal in a 1.5% agarose gel in phosphate buffer (pH 7) and blotted to nylon membranes (Hybond N, Amersham) using standard protocols. The Boehringer molecular weight marker I is used as a size standard. For Southern blot analysis, genomic DNA is isolated according to Dellaporta et al. (1983) and separated electrophoretically after endonucleolytic digestion. DNA fragments are transferred to nylon membranes (Hybond N, Amersham) according to standard procedures. Hybridization and washing of Northern and Southern blots and the filters with the YAC library is performed according to Church and Gilbert (1984). Probes are labeled with $[\alpha\text{-}^{32}P]$-dATP by random prime DNA polymerization (Feinberg and Vogelstein, 1983) and exposed to X-ray sensitive film (Kodak X-OMAT AR).

Hybridization of Northern blots using total RNA prepared from 2-week-old seedlings with TSI-A of mom1 visualizes four major transcripts with sizes of approximately 5000, 4700, 2500 and 1250 nucleotides. A TSI-B probe detects mainly two transcripts of 5000 nt and 2500 nt. Interestingly, the polyadenylated fraction of mom1 RNA contains only the transcripts of 5000 nt and 2500 nt hybridizing to both cDNA probes (TSI-A and TSI-B). From the sizes of TSI transcripts detected it is obvious that both TSI clones represent only partial cDNAs. TSI expression is meiotically heritable and persists through 6 selfed generations of mom1 with the same pattern of transcripts.

To examine TSI expression in other genotypes known to affect gene silencing, total RNA of several Arabidopsis mutant and transgenic strains known to be affected in gene silencing is probed with TSI-A. All the som mutants som1 to som8, described by Mittelsten Scheid et al (1998) to be impaired in the maintenance of transcriptional silencing similar to mom1, show a high level of TSI-A expression. The mutation ddm1, originally identified to have decreased DNA methylation (Vongs et al. 1993), and later revealed to release transcriptional gene silencing from different loci (Mittelsten Scheid et al, 1998; Jeddeloh et al., 1998) also shows a high level of TSI-A expression. TSI-A expression is also expressed in a transgenic line described by Finnegan et al (1996) which shows decreased DNA methylation due to overexpression of DNA methyltransferase antisense mRNA as well as in a further Arabidopsis mutant affected in the DNA methyltransferase gene (said mutant is referred to as ddm2 and has been provided by Eric Richards). Moreover, the silencing mutants hog1 and sil1, but not sil2 described by Furner et al (1998) express sequences hybridizing to TSI-A. Importantly, mutations affecting posttranscriptional gene silencing such as sgs1 and sgs2 described by Elmayan et al (1998) and egs1 described by Dehio and Schell (1994) do not express RNA which hybridizes to TSI-A.

Comparison of patterns of TSI-A expression in the different genotypes reveals genotype specific differences in the stochiometry of the different RNA species. mom1 plants reveal a different expression pattern of TSI-A and TSI-B as compared to som1 plants. These results indicate that a particular genetic deficiency in the transcriptional silencing system leads to a differential but specific activation of TSI templates. However, we observe variation in these activation patterns between different sources of plant material and different RNA preparations. Therefore, it is possible that patterns of TSI expression are more flexible and probably also controlled by still unknown factors acting in the mutant background, or by different stabilities among the transcript populations.

TSI-A and TSI-B are used as probes for Southern blots to determine the source of TSI transcripts and the organization of their template(s). The blots reveal that multiple copies of TSI-A- and TSI-B-homologous sequences are present in the genome of Arabidopsis. Copy numbers are assessed by reconstruction experiments to approximately 130–300 copies of TSI-A.

To examine the degree of evolutionary conservation of the TSI arrangement, DNA of five Arabidopsis ecotypes (Zuirich, Columbia, Landsberg erecta, Wassilevskija, C24) is compared by Southern blot analysis and hybridization to the TSI-A probe. Genomic DNA is digested with DraI that has a single recognition site within TSI-A and SspI that does not cut within TSI-A. A significant conservation of the TSI-A pattern among different ecotypes is observed, with two main DraI repeats of 4 kb and 1.3 kb and two major SspI fragments of 11 kb and 4 kb. Some minor differences specific for a particular ecotype indicate a limited genetic polymorphism within TSI-A. Probing the same membrane with TSI-B reveals complex banding patterns different in each ecotype which might indicate a lower degree of conservation for TSI-B, although the differences of the Southern blot patterns between TSI-A and TSI-B can also be explained if TSI-A is an internal part of a longer repeated element, and TSI-B is located proximal to a flank between repeated elements and variable single copy DNA regions.

After hybridizing TSI-A and TSI-B to the CIC YAC library covering 4 genome equivalents and 92% of the Arabidopsis genome sixty-two CIC clones out of 1152 turn out to hybridize with the TSI-A probe. Twenty-six of these contain also the pericentromeric 180-bp-repeat, 7 contain 5S RNA genes known to be located in the vicinity of a centromere, and 16 clones contain other markers that map close to centromeres. Only 4 of these clones map outside of centromeric regions. Similar mapping of TSI-B results in hybridization to all TSI-A positive CIC clones, with additional 7 clones hybridizing to TSI-B only. Thus both TSI repeats are concentrated in the pericentromeric regions of *Arabidopsis* chromosomes.

After hybridizing TSI-A and TSI-B to a cDNA library prepared with RNA isolated from mom5 mutant plants, 22 hybridizing clones are further analyzed by sequence analysis. RNA is isolated from 2-week-old seedlings of the mom1 mutant plant according to Goodall et al. (1990). The cDNA library is prepared using the Uni-ZAP XR library construction kit (Stratagene) according to the manufacturer's protocol. cDNA fragments larger than 500 bp are selected using the cDNA size fractionation columns from Gibco. 7 clones contain SEQ ID NO: 7 TSI-A-15), 5 clones contain SEQ ID NO: 8 (TSI-A-2) part of which is identical to SEQ ID NO: 4. CL Example 3

Database Searches

Sequence analysis is perfomed using the GCG software (Wisconsin Package Version10.0, Genetics Computer Group (GCG), Madison, Wis.). For identity searches, GenEMBL, the *Arabidopsis thaliana* Kazusa Aragidopsis opening site (KAOS and Swissprot are used. Peptide sequences are analysed by GeneQuiz or Expasy.

Searches within the genomic sequence databases GenEMBL, *Arabidopsis thaliana* Database, and KAOS confirm the presence of multicopy sequences related to TSI-A and TSI-B, which are distributed over all five chromosomes of *Arabidopsis thaliana*. Importantly, very often single BAG clones contain sequences homologous to both cDNA clones. In some cases, TSI-A and TSI-B related sequences are found more than once on the same BAC clone, suggesting that TSI-A and TSI-B belong to a clustered repetitive element.

The significant sequence heterogeneity between the cDNA classes and duplicates of the 5' and 3' extensions of TSI-A indicate that they originate from different activated repeats. To facilitate the data base search for a possible genomic template of the 5000 nt transcript among the multiple related copies, the overlapping cDNA sequences are combined to form a continuous 4860 bp sequence of "virtual" cDNA (SEQ ID NO: 9) which is used to search the *Arabidopsis* genomic sequence databases. A particular BAC clone (TAMU BAC T6C20, accession number AC005898) has 91% identity to the combined cDNA sequence. Further, the search uncovers a chromosomal DNA stretch (BAG F7N22, accession number AF058825) 99% identical to the abundant cDNA A-15 of Example 2 (SEQ ID NO: 7). The genomic sequence of the transcribed region 5' to the region defined by SEQ ID NO: 7 is given in SEQ ID NO: 27. It is identical to nucleotides 65081–68202 of BAC F7N22. Both sequences are located at the pericentromeric region of chromosome five. The TSI sequence defined by nucleotides 65080 to 70370 on BAC F7N22 is 54% identical to the retrotransposon-like repeat named Athila. The identity of this sequence as a retrotransposon is deduced from *Arabidopsis* genome sequences around heterochromatic regions that are marked by the presence of 180 bp satellite repeats. The 10.5 kb sequence of Athila has several characteristics of a retroelement, like long terminal repeats (LTR), a polypurine track (PPT) and a primer binding site (PBS) for tRNA priming of the reverse transcriptase, but its open reading frames do not share homology with proteins known to be involved in transposition.

The TSIs map to the 3' terminal part of Athila. TSI-A covers a part of the 3' non-coding region of the putative retrotransposon and TSI-B corresponds to the PPT and a part of the 3' LTR. The sequence of the 5' TSI-A extension encodes a possible open reading frame of 648 amino acids length (SEQ ID NO: 10) with 51% identity to 604 amino acids of the ORF2 deduced for Athila. The sequence coding for this ORF is also present on the TAMU BAC T6C20, however, the ORFs encoded by the two cDNAs clone a (SEC ID NO: 1) and clone b (SEQ ID NO: 2) and the BAC are interrupted by translational stop codons after 398 amino acids (clone a), 83 amino acids (clone b) and 46/465/496/499/549 amino acids respectively (BAC T6C20). The ORF2 sequence present on BAG F7N22 is highly degenerated by five deletions of 2–31 bp and five insertions of 3–10 bp. This further supports the assumption that this sequence is derived from a putative but degenerated retrotransposon. Data base searches for proteins similar to the potential product of the 648 amino acids ORF do not yield significantly similar polypeptides neither to proteins usually encoded by retroelements nor to any other known polypeptides.

Example 4

RNAse Protection Assays

RNase protection assays are performed according to Goodall et al. (1990) with minor modifications. To assay the direction of TSI transcription, the pCR2.1 based plasmid containing the TSI-A insert is cut by EcoRI creating a fragment of 781 bp which is ligated into the vector pGEM-7Zf(+) (Promega). To map the 5' transcription start, the probe is generated by amplifying the BAC F7N22 region between positions 64929 and 65567 and inserting the product into the pGEM-7Zf(+) vector (Promega). Labeled probes are synthesized by in vitro transcription of the linearized plasmid in the presence of [$\alpha$-$^{32}$P]-UTP using T7 polymerase (Promega) or Sp6 polymerase (Boehrnger) and purified by electrophoresis (Goodall et al., 1990). Single stranded RNA is cleaved by either 4 $\mu$g RNase A and 0.6 U RNase T$_1$ (RNase A/T assay) or by 20 U RNase T, (RNase T assay). Protected fragments are separated on a denaturing 6% polyacrylamide gel. The dried gel is exposed to a Phosphorimager screen (Molecular Dynamics) and to X-ray sensitive film. To determine the polarity of TSI transcription, RNase T and RNase ANT protection assays are performed with TSI-A probes of opposite polarity. TSI-A sequences are used as probes since TSI-A is present in all transcripts detected on Northern blots. There is no evidence for protection of the probe corresponding to the sense strand. This suggests the lack of any TSI antisense RNA and a unidirectional transcription of the TSI templates. Interestingly, RNase digestions with a TSI-A antisense probe creates a complex pattern of TSI-A protected bands. This suggests that many different but related RNAs hybridize to the probe. Since a fragment of 781 nt as expected for the protection of the entire TSI-A probe is visible, it can be concluded that TSI-A is part of an activated transcript throughout and not an artifact generated by template switch during the SSH procedure. Furthermore, some of the protected TSI-A fragments are clearly more abundant than others, suggesting either a structural conservation of particular regions of TSI-A within related RNAs, or alternatively a higher abundance of certain transcript subspecies.

The sequence information of BAC F7N22 is used to determine the position of the transcription start for the longest TSI transcript. An antisense RNA probe for RNase A/T protection is produced spanning the 638 nucleotides between positions 64929 and 65567. The probe is hybridized with total RNA from ddm1, som7 and mom1. In all RNA preparations, a fragment of approximately 480 nt (±10 nt) is protected and allowes positioning of the TSI transcription start on BAC F7N22 to 65087 (±10 nt) in different mutants.

Example 5

Reverse Transcription PCR (RT PCR)

Reverse transcription is performed with 1 µg total RNA from mom1 in the presence of 1 mM dNTPs, 4–20 U RNasin (Promega), 1×AM RTase buffer (Boehringer) and 25 U AM reverse transcriptase (Boehringer) at 37° C. for 1 hour, followed by heat inactivation of the reaction mixture. As template for PCR 50 ng reverse transcribed RNA primed by gene specific antisense primers (BA-R1, BA-R2, AT-R1, and TA-R1, see below) or 100 ng genomic DNA or 100 ng cDNA are used. PCR is started with 3 min denaturation at 94° C., followed by 30 amplification cycles (denaturation at 94° C./30 sec, annealing at 62° C./30 sec, and elongation at 72° C./30 sec) in the presence of 0.2 mM dNTPs, 0.4 µM forward and reverse primers, 1×Taq DNA polymerase buffer (Boehringer) and 0.25 U Taq DNA polymerase (Boehringer). The nucleotide sequences of the primers used for RT-PCR are:

AT-F1: 5'-CGATAACATCGACCGTATTGCTCGCC-3' (SEQ ID NO:15)
AT-R1: 5'-AACTAGCTCCCATCCGTCTTCGACATCC-3' (SEQ ID NO: 16)
AT-F2: 5'-TGCATCACACCGGATTGGATTGAC-3' (SEQ ID NO: 17)
AT-R2: 5'-TGTTCCCCTGAACCATAGCAATGAGACC-3' (SEQ ID NO: 18)
BA-F1: 5'-CAAACAGACAGAGTGTGGCCCACCACC-3' (SEQ ID NO: 19)
BA-R1: 5'-AAGAGAGGGAGAAGGCAGTGGCGTGAG-3' (SEQ ID NO: 20)
BA-F2: 5'-TGCAAACCCACAGGACCAAGTCTACCC-3' (SEQ ID NO: 21)
BA-R2: 5'-ACAGATGGTGATAGCGTGAGCGGTGGC-3' (SEQ ID NO: 22)
F7-F1: 5'-TCAACCTTTTGCCCCAACAACCACTC-3' (SEQ ID NO: 23)
F7-R1: 5'-TCTCCATCCACGCTTTCCTGAATGTCC-3' (SEQ ID NO: 24)
GS-F1: 5'-GGAGAAGGAAGCTGAAAATCATAT-TGTGG-3' (SEQ ID NO: 25)
GS-R1: 5'-ATGATGATCCTAAGTCTACCCTTTTGCAC-3' (SEQ ID NO: 26)

As a positive control for the PCR reactions, the TA-F1 and TA-R1 primers are used. The reverse transcriptase region of the pol gene of *Arabidopsis* Ty1/copia-like retrotransposon family is amplified as described by Konieczny (1991) with immaterial modifications.

Since the nucleotide sequence of the TSI transcripts TSI-A and TSI-B is related to the nucleotide sequence of the 3' half of retrotransposon-like element Athila including the second ORF and the 3' LTR, we examined by RT-PCR whether transcription of the 5' part of Athila including the first ORF is activated in mom1 plants. Five primer pairs are chosen (BA-F1-BA-R1; BA-F2-BA-R1; AT-F1-AT-R1; AT-F2-AT-R2, F7-F1-F7R1) according to the sequence information about Athila and the related parts of BAG T6C20 and BAG F7N22. All primer combinations amplified the expected products from genomic template DNA, but no PCR product could be obtained from mom1 RNA, regardless, whether cDNA synthesis was started from an Athila- or BAC-specific reverse primer or from polyT-primed cDNA (data not shown). Activation of TSI therefore is limited to sequences related to the 3' part of Athila.

The two classes of isolated cDNAs share only approximately 50% identity with Athila. To directly address the question of whether Athila is expressed, RT-PCR experiments are performed with Athila-specific primers (GS-F1, GS-R1) in the TSI homologous region. However, the corresponding fragment cannot be amplified from RNA of mom1 seedlings, suggesting that only a subset of Athila-like sequences but not the Athila element itself is reactivated in the mutant background.

To investigate whether other retroelements are transcriptionally activated in mom 1, degenerated primers in a conserved region of the reverse transcriptase gene used to clone and describe the Ta superfamily of *Arabidopsis* retrotransposons (Konieczny et al., 1991) are used to investigate, if members of the Ta family are transcribed in the mutant background. Although the expected 268 bp fragment can be amplified from genomic DNA, no amplification is achieved in RT-PCR with mom1 RNA as template. This indicates, that, in spite of the TSI homology to retrotransposons, these elements are not generally activated in the mom1 mutant.

Example 6

TSI Expression After Application of Stress (Salinity, UV-C, Pathogen)

Induction of TSI upon UV-C is tested on Northern blots with RNA samples from 1 week-old-seedlings subjected to UV-C treatment of 1 kJ/m$^2$ or 5 kJ/m$^2$ which are collected at several time points within 1 hour (Revenkova et al., 1999). The effect of osmotic stress is tested on Northern blots with RNA from one-week-old seedlings that are transferred for 24 hours to medium with NaCl concentrations of 0, 0.04, 0.08 and 0.12 M (Albinsky et al., 1998). To test TSI expression upon pathogen stress, RNA of 3-week-old seedlings either mock treated or infected with *Peronospora* is analysed by Northern blot analysis. To verify the appropriate pathogen response, induction of PR1 expression is monitored by reprobing the membrane with a PR1 probe.

In young seedlings (2 weeks old) and in different tissues of mature wild type plants (roots, shoots, leaves, flowers, siliques), TSI expression cannot be detected. The application of various stress treatments namely elevated salinity, UV-C, or pathogen infection, does not activate TSI in wild type plants. TSI expression is also not detected in freshly initiated callus cultures, and transcriptional suppression of TSI is stable even after several in vitro passages of the callus culture. However, the only exception so far are cells derived from wild type *Arabidopsis* (literature) growing for a long time in suspension culture. These cells express TSI-A, indicating release of TSI silencing under these conditions.

REFERENCES

Albinsly et al, Plant J. 17: 73–82, 1999
Amedeo et at, Nature 405: 203–206, 2000
Church and Gilbert, Proc Natl Acad Sci USA 81: 1991–1995, 1984
Dehio and Schell, Proc Natl Acad Sci USA 91: 5538–5542, 1994
Dellaporta et al, Plant Mol Biol Rep. 1:19–21, 1983
Diatchenko et al, Proc Natl Acad Sci USA 93: 6025–6030, 1996

Dilkes and Feldmann, in *Arabidopsis* protocols, Methods in Molecular Biology 82 (Ed.
Martinez-Zapater and Salinas), Humana Press, Totowa, N.J., pp 339–351, 1998
Elmayan et al, *Plant Cell* 10: 1747–1757, 1998
Feinberg et al, *Anal Biochem.* 132: 6–13, 1983
Feldmann et al, in *Arabidopsis* (Ed. Sommerville and Meyerowitz), CSHL Press, New York, pp 137–172,1994
Finnegan et al, *Proc Natl Acad Sci USA* 93: 8449–8454, 1996
Furner et al, *Genetics* 149: 651–662, 1998
Goodall at, *Methods Enzymol.* 181: 148–161, 1990
Jeddeloh et at, *Genes Dev.* 12:1714–1725, 1998
Konieczny et al, *Genetics* 127: 801–809, 1991
Long and Coupland in *Arabidopsis* protocols, Methods in Molecular Biology 82 (Ed.
Martinez-Zapater and Salinas), Humana Press, Totowa, N.J., pp 315–328, 1998
Mittelsten Scheid et al, *Proc Natl Acad Sci USA.* 95: 632–637, 1998
Pellisier et al, *Plant Mol. Biol.* 29: 441–452,1995
Pereira and Aarts, in *Arabidopsis* protocols, Methods in Molecular Biology 82 (Ed.
Martinez-Zapater and Salinas), Humana Press, Totowa, N.J., pp 329–338,1998
Revenkova et al, *EMBO J.* 18: 490–499, 1999
von Stein et a!, *Nucleic Acids Res.* 25: 2598–2602, 1997
Vongs et at, *Science.* 260: 1926–1928, 1993

What is claimed is:

1. A method of selecting a plant which compared to a wild type plant is impaired in transcriptional gene silencing, comprising
   a) separately preparing RNA of a series of plants;
   b) probing said RNA preparations with a nucleic acid which comprises at least 50 nucleotide residues of a sequence that is at least 90% identical when aligned with SEQ ID NO: 27; and
   c) identifying a plant whose RNA hybridizes with said nucleic acid.

2. The method of claim 1, wherein process steps b) and c) comprise reverse transcription of the RNA and subsequent amplification of the generated DNA using oligonucleotide primers specific for SEQ ID NO:27.

3. A method according to claim 1 wherein said nucleic acid comprises at least 100 nucleotide residues of a sequence that is at least 90% identical when aligned with SEQ ID NO: 27.

4. A method according to claim 1 wherein said nucleic acid comprises at least 200 nucleotide residues of a sequence that is at least 90% identical when aligned with SEQ ID NO: 27.

5. A method of selecting a plant which compared to a wild type plant is impaired in transcriptional gene silencing, comprising
   a) separately preparing RNA of a series of plants;
   b) probing said RNA preparations with a nucleic acid which consists of SEQ ID NO: 27; and
   c) identifying a plant whose RNA hybridizes with said nucleic acid.

* * * * *

SEQUENCE LISTING

<160> NUMBER OF SEQ ID NOS: 27

<210> SEQ ID NO 1
<211> LENGTH: 2512
<212> TYPE: DNA
<213> ORGANISM: Arabidopsis thaliana

<400> SEQUENCE: 1

```
tcgccgttcc agcttcgcat actctctcac cgtctctcgt ttcactcgac cacttcacac      60
ttcgcctcaa catcttcgcc ggagtttctc gccattgtcc gtgcttccgt catctccgtt     120
cactcgacca ccggaccggc ttcaccatct ctcaactatc caccattcac tcgacctcgc     180
cattcactgc gcctccattc gtctctttac tcgactgctc ctcaaaccgc caccgtcttc     240
tctaaattcg ccgtttactc gaccacactg ttacgtctct cattcgtgta cagtcgaccg     300
ctatacccga agccacaata tcactctact cgaccgtttc actcgatcgc gtacttgact     360
ggtttagtgt gtgtgtttat ttgaactaac atattgatat ttggttttga gttacattct     420
ttttcaggga atcaatatga gcaactacag tggcgaatcc tccatggatg cggattacaa     480
cgtcgatgaa gctgaatctt ggtcaactag accagagaga gagcaacagg cttatgagag     540
cttcagagcc gagacccaac gctcagtagc tcgacgcaat gaaaggagag ctgagattgc     600
tagaggaaag agagcgatga ccagcagata tgagttgatc gacgaagata ttgacgtcga     660
gtatgagcct gagtcatggc acagagaaac aaaactgttg aacaagcctg atgaagttac     720
agtggaagag tacatcagac ttttcgagct gaacgacttc tggggagcga ggtaccctg     780 ttatgagact ctagcccagc ttaggctact ggaggacgta cagcacttat tcgagaagtg     840
ccatcttgag acgctgatgt cttacccgta cgtcgcttac aagaaggaaa caatagagtt     900
tctctccact ctgcaagtgg agttgtatca gggacttact gcagatgaac tggagagtga     960
agggttggga ttcttgactt tttcagttaa cgagcagcgt taccagctat ctatcaagag    1020
cttggaagga ttatttggtt ttcccagtgg aaagggaact aaacccaagt tcgaaaggga    1080
agagttgaag gatttgtggt taaccattgg gaacgatttg gcgctcaact ctgcaaggtc    1140
taagagcaac cagattcgaa gccctgtgat ccgctactat cagcgctcag tagcgaatgt    1200
tctgtacccc agggaatcta caggcaccgt gtctaacaca gacatggaga tgattgattc    1260
tgcactcaag ggtattctcc ggagaacaaa ggggaagaag gtcctaaagg gcgaccttaa    1320
tgatacacca ccggtcatgc ttctgttgat ccatatgtgt ggatacagga agtgggcgca    1380
caccaacggg aggaagaagg tgcgaggagc cctttgtgtg ggtggcgttg tgacaccgat    1440
```

-continued

| | |
|---|---|
| tctgattgca tgtggtgtac ctctcacgtc tccagggttt gatccgagga tgatggattt | 1500 |
| agatcacttg cgtcgttgtg agtttctgga gtacgacatg gttggcgatt tctatcgcta | 1560 |
| caaattcgag cactccctga cccgaacagc aacattttg cttccctgca tcgaggccac | 1620 |
| aaccatactt tagggtgaga acattgactt cagacctgcg cgtgattacc tctactttga | 1680 |
| gagcactcca ccgactgatg acaatgtccc tacgacggaa gctacagagg atgattttgc | 1740 |
| tgagacggat gaggataggg aggaggagta tgatacgagc atgtatcatt tcagtgagca | 1800 |
| cgtacctcca gcgcaggaga gcaagagctt gagtgaagct cacagaaaca acagtaagtt | 1860 |
| gcagaggtgg tgcaagaaac aagataggtt acttatcaag tgcttcaagg ccatcacgtt | 1920 |
| tctaacggac aagataagtt gcttctcttc taccacagct attccgcagg gagagcgtcc | 1980 |
| tcaggacatg ccttcgaaga gatatgacgc gccagggcca agtcatcaca ggcctgagcc | 2040 |
| aagtcaccac aggcctgagc ctagtgaccg agtagtacca ccagtccctg caaggcattc | 2100 |
| atcattcgag cctcgggagc tcgggagaaa gaagaaggct gcactcgcta ggtctggcag | 2160 |
| caggagtaga cgacttctcc agtcccgtag cttacgcgac cgcggtgctg gccgcagcag | 2220 |
| aagaagagag gtcgagtatc atcagagcgg tgctggccgc ggcgaaggag cagaggtcga | 2280 |
| gtaccccag ggggaagctg agacacaaca gggagattct tcgatggcct gggagcaatc | 2340 |
| acaggcagct attgacgacc aactccgctc cttcttccac tgaggtatgc acctcactcc | 2400 |
| accattgtaa tataccatct cttgtttttt attttgtttt tgtgatgtgt tttgtcctga | 2460 |
| gtactctctt ccaaatttgg tcacacagtg gactgtgtga tttaagtttg gg | 2512 |

<210> SEQ ID NO 2
<211> LENGTH: 1997
<212> TYPE: DNA
<213> ORGANISM: Arabidopsis thaliana

<400> SEQUENCE: 2

| | |
|---|---|
| ccgggcaggt caacaggctt atgagagctt tagagctgag acccaacgct cagtagctcg | 60 |
| acgcaatgaa aggagagctg agattgctag aggaaagaga gcaatgacca gcagatatga | 120 |
| gttgatcgac gaagatattg acgtcgagta tgaacctgaa tcatggcaca gagaaacgaa | 180 |
| gctgttgaac aagcccgatg aagttacagt agaggagtac atcagacttt tcgagctgaa | 240 |
| cgacttctag ggaacgaggt accctgtta tgagacttta gcccagctgg ggctactgga | 300 |
| ggacgtacat cacttattcg agaagtgcca tctggagacg ctgatgtctt acccgtacgt | 360 |
| cgcttacaag aaggaaacaa tagagtttct ctccactctg caagtggaga tgtatcaggg | 420 |
| acttactgca gatgagctgg agagtgaagg gttggggttc ttgacttttt cagttaacga | 480 |
| gcagcgttac cagctatcta tcaagagctt ggaaggatta tttggttttc aagtggaaa | 540 |
| gggaactaaa cccaagttcg agagggaaga gttgaaagat tgtggttaa ccattgggaa | 600 |
| cgatttggca ctcaactctg caaggtctaa gagcaaccag attcgaagcc tgtgatccg | 660 |
| ctactatcag cgctcagtag cgaatgttct gtaccccagg gaatctacag catcgtgtc | 720 |
| taacacagac atggagatga ttgatgttgc actcaagggc attctccgga gaacaaaggg | 780 |
| gaagaaggtc ctaaagggcg accttaatga tacaccaccg ttatgcttc tgttgatcca | 840 |
| cctgtgtgga tacaggaagt gggcgcacac caacgagaag aagaaggtgc gaggagccct | 900 |
| ttgtgtaggt ggcgttgtga caccgattct gattgcatgt ggtgtacctc tcacgtctcc | 960 |
| aggtttgat ccgaggatga tggatttaga tcacttgcgt cgttgtgagt ttctagagta | 1020 |
| cgacatggtt ggcgatttct atcgctacaa attcgagcac tccctgaccc gaacagccaa | 1080 |

-continued

```
cattttgctt ccctgcatcg aggccacaac catacttcag ggtgagaaca ttgacttcag    1140
acctgcgcgt gattacctct actttgagag cgctccaccg actgatgaca atgtccctac    1200
gacggaagtt acagaggatg atattgctga gacggatgag gatagggagg aggagtatga    1260
tacgagcatg tatcatttca gtgagcacgt acctccagcg cgggagagca agagcttgag    1320
tgaagctcac agaaacaaca gtaagttgca gaggtggtgc aagaaacaag ataggctact    1380
tatcaagtgc ttcaaagcca tcacgttcct gacggacaag ataagctgct tctcttctac    1440
cacagctatt ccgcagggag agcatcctca ggacatgcct tcaaggagat atgacgcgcc    1500
agcgccaagt catcacaggc ctgagccaag tcaccacagg cctgagccta gtgaccgagt    1560
agtcccacca gtccctgcaa ggcattcatc attcgagcct cgggagctcg ggagaaagaa    1620
gaaggctgca ctcgctcggt ctggcagcag gagtacacga cttctacagt cccgtagctt    1680
acgcgaccgt ggtgctggcc gcagcagaag aagagaggtc gagtatcatc agagcggtgc    1740
tggccgcgac gaaggagcag aggtcgagta ccccacgggg aagctgagac acaacaggga    1800
gattcttcga tggcctggga gcaatcacat gcagctattg acgaccaact ccgctccttc    1860
ttccactgag gtatgcacct cactccacca ttgtaatata ccatctcttg ttttatttt     1920
gttttttgtga tgtgttttgt cctgagtact ctcttccaaa tttggtcaca cagtggactg    1980
tgtgatttaa gtttggg                                                    1997

<210> SEQ ID NO 3
<211> LENGTH: 1682
<212> TYPE: DNA
<213> ORGANISM: Arabidopsis thaliana

<400> SEQUENCE: 3
cttatattat gggttgggat gtgtttaaag aaaagggga attcattgtt gataaggaaa        60
gggaaagaat tctaggggaa gtaagctaaa gaagttagaa aaaatctagt aaaggttttg      120
ggaatgttaa agaaaagaat gaggttcttg ttagctaaag aataagggtt aaaagccttt      180
ggttttaaag attaaaaaaa aaacaggaac cttagttgtt aaagaaatcc aaacccgcta      240
gatgtatcaa gagcgttgag aaagcttctc ctagagttaa gagaaaagaa aagaatgata      300
tgaaaaagag tttgaaagat tcatgagtgc aagggggtaga gttaagttgg gacaggagtt      360
ggttttacca ttagaacttc attgttatac tctgggtaga tgggatctta tctctgtatg      420
cataatttgg gacttacctt tagcattcta ctaaagctca atcattcttg agggatcccc      480
tgttacttaa gcctattcta taagggacca tctttgtctc ttgaccttca ccttggccga      540
atgagttcat tgatgatgca ttgcttgatt cgcgttccag aactaatgaa tgttaaaggg      600
attggtagat ttgaaagcat gtgtaggtcg agtataagag acggattgat tgaaaacaag      660
gcatggctaa cgttttttgag tagaattcaa tcatatcgca tcttagaact accaacttgg      720
acattgattt tatttgctct atcatatgct ttggttttga gtccccgcct tcactcctct      780
ccttcaacta tgtcttctta tttgcttgag ggcaagcaaa gactaagttt gagggagttg      840
atatgtctat aatttgcatg ttttcagtgt ccattcatca tcgttttgag tccagttcg       900
tatcattcat cactgtttta tatcatttct catcattctt gcatactttg catgattagg      960
ataactttgc atacatattg catttctgag ttgttttcag gtgatttgga gctgtttgca     1020
agcaaattgg aagaaatgag ccagaaccag aagacatact cgaccccctag gtcgagtgac    1080
tttggggcca ttcttcccac atactcggcc cccaggtcga gtgactttgg agccattctt    1140
```

-continued

```
cccatccact cgaccaccgg gtcgagtaac cttagctcag gccactcgat gacactactc    1200
gaccccaggt cgagtatcac ttcgccacac cacctgacaa cactcgacca atcactctac    1260
caagttactc gaccccctgg tcgagtatca tcactcacca ccatcagcat cactcgaccg    1320
gacactcgat cacgtcttca cagtctactc aaatccgcag tcaaccagac aagctgagca    1380
caaggaagag aagaggagaa acaaagtgc ttggaagcgg cctggacctc catcggatca     1440
cgaagcccat ctcggcccat tatctctcta tgggccgagc gattaggtta ttggcccgtc    1500
tactatcatt ttatttcgtt ttgtataaat agatgtctta gggttttgtc ctgagacatc    1560
tagtcgacat tgagtttttt ttgcttcagt tttattttct gttctactct gctgcgccgc    1620
ttttgcttct gcaacctgta attcgagatt tttccaagtt attcagattc cgcatttgat    1680
tt                                                                   1682

<210> SEQ ID NO 4
<211> LENGTH: 1652
<212> TYPE: DNA
<213> ORGANISM: Arabidopsis thaliana

<400> SEQUENCE: 4
cttatatcat gggtttggat cagtttaaaa aaaaaaaagg gtgaattcat tgttgataag      60
gaaagggaaa gaattctagg ggaagtaagc taaagaagtt agaaaaaaaa aaatctagta     120
aaggttttgg gaatgttaaa gaaaagaatg aggttcttgt tagctaaaga agaagggtta    180
aaagcctttt gttttaaaga ttaaaaacag gaaccttagt tgttaaagaa atccaaatac    240
gctagatgta tcagagtgtt gagaaagctt ctcctagagt taagagaaaa gaaaagaatg    300
atatgaaaaa gagtttgaaa gattcatgag tgcaaagggt agagttaagt tcttgtattg    360
ggactggagt tgggattacc attagagctt cattgttata ctatgggtag atgggatttt    420
atctctgtat gcataacttg ggacttacct ttagcattct actaaagctc aatcattctt    480
gagagatccc ctgttactta agcctattct gtaagggacc atctttgtct cttgaccttc    540
accttagcca aatgagttca ttgatgatgc attgtttgat tcacgttcca gaactaatga    600
atgttaaagg gattggtaga tttgaaagca tgtgtaggtc gagtataaga gacggattga    660
ttgataacaa ggcatggcta acgttttcga gtaaaattca atcatatcgc atcttagaac    720
taccaacttg gacattgatt ttatttgctc tatcagatgc tttggttctg agtccccacc    780
ttcaaaccct ccttcaact atgtcttctt atttgcttga gggcaagcaa agactaagtt     840
tgggggagtt gatatgtcta taatttgcat gttttcagtg tccattcatc atcgttttga    900
gtccagtttc gtatcattca tcactgtttt atatcatttc tcatcattct tgcatacttt    960
gcatgattag gatagctttg tatacatatt gcatttctga gttgttttta ggtgatttgg   1020
agctgtttgc gagcaaattg gaagaaacga gccagaacaa gaagccatac tcgacccct    1080 ggtcgagtga ctttggagcc attcttccca tctactcgac ccgggggtcg agtaacctca    1140
gctcaggcca ctcgatgacg ccactcgtcc cccctggtcg agtatcactt cgccacacca    1200
cctgaccaca ctcggccgtt cactctacca cgttactcga cccccctggtc gagtatcatc   1260 actcaccacc aacaccatca ctcgaccggg cactcgatca catcttcata gtctactcaa    1320
atccgcactc aaccagacaa gctgagcaca aggaagagaa gaggagaaga caaagtgttt    1380
ggaagcggcc tggacctcca tcggatcacg aagaagccca tctcggccca ttatcattct    1440
atgggccggg cgattaggtt attggcccgt ctactatcat tttatttcgt tatgtataaa    1500
tagatgtctt agggttctgt accaggacat ctagtcgaca ttgagttttt ttgcttcagt    1560
```

```
tttattttct gttttctctg ctgcgccgct tttgtttctg caacctgtaa ttcgagattt     1620
ttccaagtta ctcagattcc gcatttgatt tc                                   1652

<210> SEQ ID NO 5
<211> LENGTH: 903
<212> TYPE: DNA
<213> ORGANISM: Arabidopsis thaliana

<400> SEQUENCE: 5
tactctcttc caaatttggt cacacagtgg actgtgtgat ttaagtttgg gggagggctc       60
aggaagtgtg tgttgcattg tataatcttg agtttgcatt catctaaggc atagaaaaac      120
caaaaaaatt gaaaaattcc agaaaatgat tcacaaaaa tagagtgttc atgtagttgc      180
attgcattta ggatcgagtt tagagtgttt cgtttaggat tgttgcatat gcataggga       240 taataatgag atagccttgt aagcattttg gttcaccaga taagctcagt gccctcgttg      300
ttagttgttt gatgcgttgt cattgaaatt gaagtaagaa ctgcacgatg cctagattgc      360
tctactcgac cacactgtta ggatctgata tcattcccta tcaatttgaa cttgaatctg      420
atttagaatt atcatgtctt ggcatcgaat ttgaactcat ggataccta aaatacttgg       480 attttcttac tcattttaac cactcttgtt gatccaagta gctgactctc cttattagag      540
cagttaaccc atacccaaac ctgaactttc tttcaagccc tatatcactt gtgagtgttt      600
gtgaggtctt atttcgattg agcttggtag aaagtgttag gttcgtaacg acagagatag      660
tgtctcatgt agttctagtt tgcgttcttc agactggata ggactaggtg ggcgcttata      720 tcatggggttg ggatgtgttt aaaagaaaag agggaatcta ttgttgatga ggaaagggaa      780
agaattccag gggaagtaag ctaaagaagt tagaaaaaaa atctagtaaa ggttttggga      840
atgttaaaga aaagaatgag gttcttgtta gctaaagaag aagggttaaa agcctttggt      900
ttt                                                                    903

<210> SEQ ID NO 6
<211> LENGTH: 614
<212> TYPE: DNA
<213> ORGANISM: Arabidopsis thaliana

<400> SEQUENCE: 6
gagggcaagc aaagactaag tttgggggag ttgataagtg tgtattttgc atgttttgag       60
catccatttg tcatcacttt agcatcatat catcactgtt ttataccatt tcacatcatt      120
tgtcatcact ttgcatgttt aggatagttt tgcatgcatg ttgcatattt gcgttgattt      180
caggtgattt ggagctgttg acgagctatc tggaagaagc agacctgatc atgacaaacc      240
actcgaccca gaggtcgagt aggagcttca agatctcaag agactactcg acaaccaggt      300
cgagtagagc acatcaccac ttcacctcac cactcgaccc cgaggtcgag tgccatcatc      360
tccatcacca gacggtcact cgatcacttc actcgacctt gaggtcgagt gtcttcacct      420
ccatcatcag acaaccactc gacctcctca ctccacctag aggtcgagta tctccatctt      480
accactcgac tgcatactcg atgacaagct tcagagcctt cttaattccg cactcaacca      540
gacactcgag cacaaggaag aaaagaagac tccagctatt cactcgagct ctcactcgac      600
cacgtgggtc gagt                                                        614

<210> SEQ ID NO 7
<211> LENGTH: 1956
<212> TYPE: DNA
```

<210> SEQ ID NO 7
<211> LENGTH: 1956
<212> TYPE: DNA
<213> ORGANISM: Arabidopsis thaliana
<220> FEATURE:
<221> NAME/KEY: misc_feature
<222> LOCATION: (1)..(1956)
<223> OTHER INFORMATION: n = a, t, c, or g

<400> SEQUENCE: 7

```
ttttggttca ccggattaac tcagtgctct cgttgctagt tgtgtgttgc gtagtgaatg      60
aatttgaaag aaaactgaac catgcctaga ttgctctact cgaccacact gtcatgatct     120
gataccattc cctatcaatt tgaacctgaa tttgatcttt aattatcatg tctgcatcaa     180
atttgaactc atggataccc taaaatactt ggattttctt attcattttg atcactcttg     240
ttaatccaag tagctgactc tccttattag agcagttaac ccgaacccaa acctagactt     300
tttttcaagc cttatatcac tcgtgagggt ttgtgaggtc ttattccgat tcagcttggt     360
agaaagtgtt aggttcgtaa cgacagagat agtgnctcat gtagttctag ttcgcatttt     420
ttggactaga taggactggg tgggcgctta tactttaggt tgggatgngt ttaaaagaaa     480
aaaaagggg ttgattcatt gatgagaaaa ggtaaaagac tctaggtgaa gtaagataaa     540
gaagcagaaa aggtctagta aaggttttgg gatttgtaaa aaaagaaag agttcttgtt     600
agctattgaa gatgggcaaa agccctcggt tttaaaatgt taaaaacagg aaccttagtt     660
gttaaagaaa tccaaatccg ctagatgtat caaagtgttg agaaagcttt tcctagagtt     720
aagagaaaag aaaagaatga ttagaaaaag ggcttaaagg attcatgaat gcaaagggta     780
gaggtaagtt cttatactgg gattggagat gggattacca ttagagcttc atctgatata     840
ctctaggtag atgggatctt atctctgcat gcatagtttg ggacttacct ttagcattct     900
actaaagctt aatcattttt tgagagatcc cctgttactg aagcctattc tgtaagggac     960
catctttgtc tcttgacctt ttaccttagc caaatgagtt cattgatgat gcattgcttg    1020
attcacgttc cagaactaat gaatgttaaa gggattggta gatttgaaaa catgtgtagg    1080
tcgagcatat gagtcggatt gattgatagt aaggcatggc taaagttttt cagtagaatt    1140
cgatcatatc gcagcttaga actatcaact tggacattga tttcatttgg tttatctagt    1200
gctttggctc tgagtccccg atttcaaacc tcacctctag cttgttctta attgtttgct    1260
tgagggcaag caaagactaa gtttggggga gttgataagt gtgtattttg catgttttga    1320
gcatccattt gtcatcactt tagcaccata tcatcactat tttataccat ttctcatcat    1380
ttgtcatcac tttgcatgtt taggatagtt ttgcatgcat gtggcatatt tgtgttgttt    1440
tcaagtgatt cggagctgtt gaagaactaa ttggaagaag cggacctgat catgccaaac    1500
cactcgacct caggtcgagt agacgcttca cgacctcaac acaccactcg accacctggt    1560
cgagtgtagg acttcaccac ttcacctcat cactcgaccc cctggccgag taccccacga    1620
gagtcactcg atcacttcac tcgacccca ggtcgagtgt cttcacctcc accacctgac    1680
catcactcga tcacacgact ctacctggaa gtcgagtatc accatcacca ccactcgact    1740
acatacttga tgtcgagctt cagagtcttc tccattccgc actcaaccag acactcgagc    1800
acaaggaaaa aaagaagatt ctagcttatc actcgacctc tcactcgacc acctgggtcg    1860
agtacagttc ttaatccgtc tcaatactgc gtcgttttga gtattagggt ttcggaatat    1920
ttttgctata agtagcacgt actttacatt ttcgag                              1956
```

<210> SEQ ID NO 8
<211> LENGTH: 2105
<212> TYPE: DNA
<213> ORGANISM: Arabidopsis thaliana

<400> SEQUENCE: 8

```
ttagcattttt ggttcactag ataaactcag tgccctcgtt gttagttgtc tgatgcatac      60
tcaatgaaat tgaagtaaaa ctgcaccatg cctagattgc tctactcgac cacactgtta     120
ggatctgata ccattcccta tcaatttgaa cttgaatctg atttagaatt atcatgtctt     180
gccatcgaat ttgaactcat ggataccctg aaatacttgg attttcttac tcattttaac     240
cactcttgtt aatccaagta gctgactctc cttattagag cagttaaccc gaatccaaac     300
ctaatctttc tttcgagccc tatatcactt gtgagtgttt gtgaggtctt atttcaattg     360
agcttggtag aaagtgttag gttcgtaacg acagagatag tgtctcatgt agttctagtt     420
cgcgttttt  ggactggata ggactaggtg ggcgcttata tcatgggttt ggatcagttt     480
aaaaaaaaaa aagggtgaat tcattgttga taaggaaagg gaaagaattc taggggaagt     540
aagctaaaga agttagaaaa aaaaaatct  agtaaaggtt ttgggaatgt taaagaaaag     600
aatgaggttc ttgttagcta aagaagaagg gttaaaagcc ttttgtttta aagattaaaa     660
acaggaacct tagttgttaa agaaatccaa atacgctaga tgtatcagag tgttgagaaa     720
gcttctccta gagttaagag aaaagaaaag aatgatatga aaaagagttt gaaagattca     780
tgagtgcaaa gggtagagtt aagttcttgt attgggactg gagttgggat taccattaga     840
gcttcattgt tatactatgg gtagatggga ttttatctct gtatgcataa cttgggactt     900
acctttagca ttctactaaa gctcaatcat tcttgagaga tccctgtta  cttaagccta     960
ttctgtaagg gaccatcttt gtctcttgcc ttcaccttag ccaaatgagt tcattgatga    1020
tgcattgttt gattcacgtt ccagaactaa tgaatgttaa agggattggt agatttgaaa    1080
gcatgtgtag gtcgagtata agagacggat tgattgataa caaggcatgg ctaacgtttt    1140
cgagtaaaat tcaatcatat cgcatcttag aactaccaac ttggacattg attttatttg    1200
ctctatcaga tgctttggtt ctgagtcccc accttcaaac ctctccttca actatgtctt    1260
cttatttgct tgagggcaag caaagactaa gtttggggga gttgatatgt ctataatttg    1320
catgttttca gtgtccattc atcatcgttt tgagtccagt ttcgtatcat tcatcactgt    1380
tttatatcat ttctcatcat tcttgcatac tttgcatgat taggatagct ttgtatacat    1440
attgcatttc tgagttgttt ttaggtgatt tggagctgtt tgcgagcaaa ttggaagaaa    1500
cgagccagaa caagaagcca tactcgaccc cctggtcgag tgactttgga gccattcttc    1560
ccatctactc gacccggggg tcgagtaacc tcagctcagg ccactcgatg acgccactcg    1620
tcccccctgg tcgagtatca cttcgccaca ccacctgacc acactcggcc gttcactcta    1680
ccacgttact cgacccctg  gtcgagtatc atcactcacc accaacacca tcactcgacc    1740
gggcactcga tcacatcttc atagtctact caaatccgca ctcaaccaga caagctgagc    1800
acaaggaaga gaagaggaga agacaaagtg tttggaagcg gcctggacct ccatcggatc    1860
acgaagaagc ccatctcggc ccattatcat tctatgggcc gggcgattag gttattggcc    1920
cgtctactat catttttattt cgttatgtat aaatagatgt cttagggttc tgtaccagga    1980
catctagtcg acattgagtt ttttttgcttc agttttattt tctgttttct ctgctgcgcc    2040
gcttttgttt ctgcaacctg taattcgaga ttttttccaag ttattcagat tccgcatttg    2100
atttc                                                                2105
```

<210> SEQ ID NO 9
<211> LENGTH: 4860
<212> TYPE: DNA

```
<213> ORGANISM: Artificial Sequence
<220> FEATURE:
<223> OTHER INFORMATION: Description of Artificial Sequence: Virtual TSI

<400> SEQUENCE: 9
tcgccgttcc agcttcgcat actctctcac cgtctctcgt ttcactcgac cacttcacac      60
ttcgcctcaa catcttcgcc ggagtttctc gccattgtcc gtgcttccgt catctccgtt     120
cactcgacca ccggaccggc ttcaccatct ctcaactatc caccattcac tcgacctcgc     180
cattcactgc gcctccattc gtctctttac tcgactgctc ctcaaaccgc caccgtcttc     240
tctaaattcg ccgtttactc gaccacactg ttacgtctct cattcgtgta cagtcgaccg     300
ctatacccga agccacaata tcactctact cgaccgtttc actcgatcgc gtacttgact     360
ggtttagtgt gtgtgtttat ttgaactaac atattgatat ttggttttga gttacattct     420
ttttcaggga atcaatatga gcaactacag tggcgaatcc tccatggatg cggattacaa     480
cgtcgatgaa gctgaatctt ggtcaactag accagagaga gagcaacagg cttatgagag     540
cttcagagcc gagacccaac gctcagtagc tcgacgcaat gaaaggagag ctgagattgc     600
tagaggaaag agagcgatga ccagcagata tgagttgatc gacgaagata ttgacgtcga     660
gtatgagcct gagtcatggc acagagaaac aaaactgttg aacaagcctg atgaagttac     720
agtggaagag tacatcagac ttttcgagct gaacgacttc tggggagcga ggtacccctg     780
ttatgagact ctagcccagc ttaggctact ggaggacgta cagcacttat tcgagaagtg     840
ccatcttgag acgctgatgt cttacccgta cgtcgcttac aagaaggaaa caatagagtt     900
tctctccact ctgcaagtgg agttgtatca gggacttact gcagatgaac tggagagtga     960
agggttggga ttcttgactt tttcagttaa cgagcagcgt taccagctat ctatcaagag    1020
cttggaagga ttatttggtt tcccagtgg aaagggaact aaacccaagt tcgaaaggga    1080
agagttgaag gatttgtggt taaccattgg gaacgatttg gcgctcaact ctgcaaggtc    1140
taagagcaac cagattcgaa gccctgtgat ccgctactat cagcgctcag tagcgaatgt    1200
tctgtaccc aggaatcta caggcaccgt gtctaacaca gacatggaga tgattgattc    1260
tgcactcaag ggtattctcc ggagaacaaa ggggaagaag gtcctaaagg gcgaccttaa    1320
tgatacacca ccggtcatgc ttctgttgat ccatatgtgt ggatacagga agtgggcgca    1380
caccaacggg aggaagaagg tgcgaggagc cctttgtgtg ggtggcgttg tgacaccgat    1440
tctgattgca tgtggtgtac ctctcacgtc tccagggttt gatccgagga tgatggattt    1500
agatcacttg cgtcgttgtg agtttctgga gtacgacatg gttggcgatt tctatcgcta    1560
caaattcgag cactccctga cccgaacagc caacattttg cttccctgca tcgaggccac    1620
aaccatactt tagggtgaga acattgactt cagacctgcg cgtgattacc tctactttga    1680
gagcactcca ccgactgatg acaatgtccc tacgacggaa gctacagagg atgattttgc    1740
tgagacggat gaggataggg aggaggagta tgatacgagc atgtatcatt tcagtgagca    1800
cgtacctcca gcgcaggaga gcaagagctt gagtgaagct cacagaaaca acagtaagtt    1860
gcagaggtgg tgcaagaaac aagataggtt acttatcaag tgcttcaagg ccatcacgtt    1920
tctaacggac aagataagtt gcttctcttc taccacagct attccgcagg gagagcgtcc    1980
tcaggacatg ccttcgaaga gatatgacgc gccaggggcca agtcatcaca ggcctgagcc    2040
aagtcaccac aggcctgagc ctagtgaccg agtagtacca ccagtccctg caaggcattc    2100
atcattcgag cctcgggagc tcgggagaaa gaagaaggct gcactcgcta ggtctggcag    2160
caggagtaga cgacttctcc agtcccgtag cttacgcgac cgcggtgctg gccgcagcag    2220
```

-continued

```
aagaagagag gtcgagtatc atcagagcgg tgctggccgc ggcgaaggag cagaggtcga   2280 gtaccccag ggggaagctg agacacaaca gggagattct tcgatggcct gggagcaatc   2340
acaggcagct attgacgacc aactccgctc cttcttccac tgaggtatgc acctcactcc   2400
accattgtaa tataccatct cttgttttt atttttgtttt tgtgatgtgt tttgtcctga   2460
gtactctctt ccaaatttgg tcacacagtg gactgtgtga tttaagtttg ggggagggct   2520
caggaagtgt gtgttgcatt gtataatctt gagtttgcat tcatctaagg catagaaaaa   2580
ccaaaaaaat tgaaaaattc cagaaaatga tttcacaaaa atagagtgtt catgtagttg   2640
cattgcattt aggatcgagt ttagagtgtt tcgtttagga ttgttgcata tgcataggg   2700 ataataatga gatagccttg taagcatttt ggttcaccag ataagctcag tgccctcgtt   2760
gttagttgtt tgatgcgttg tcattgaaat tgaagtaaga actgcacgat gcctagattg   2820
ctctactcga ccacactgtt aggatctgat atcattccct atcaatttga acttgaatct   2880
gatttagaat tatcatgtct tggcatcgaa tttgaactca tggatacccct aaaatacttg   2940 gattttctta ctcattttaa ccactcttgt tgatccaagt agctgactct ccttattaga   3000
gcagttaacc cataccaaa cctgaacttt ctttcaagcc ctatatcact tgtgagtgtt   3060
tgtgaggtct tatttcgatt gagcttggta gaaagtgtta ggttcgtaac gacagagata   3120
gtgtctcatg tagttctagt ttgcgttctt cagactggat aggactaggt gggcgcttat   3180
atcatgggtt gggatgtgtt taaaagaaaa gagggaatct attgttgatg aggaaaggga   3240
aagaattcca ggggaagtaa gctaaagaag ttagaaaaaa aatctagtaa aggttttggg   3300
aatgttaaag aaaagaatga ggttcttgtt agctaaagaa gaagggttaa aagcctttgg   3360
ttttaaagat taaaaaaaa acaggaacct tagttgttaa agaaatccaa acccgctaga   3420
tgtatcaaga gcgttgagaa agcttctcct agagttaaga gaaaagaaaa gaatgatatg   3480
aaaaagagtt tgaaagattc atgagtgcaa agggtagagt taagttggga caggagttgg   3540
ttttaccatt agaacttcat tgttatactc tgggtagatg ggatcttatc tctgtatgca   3600
taatttggga cttaccttta gcattctact aaagctcaat cattcttgag ggatcccctg   3660
ttacttaagc ctattctata agggaccatc tttgtctctt gaccttcacc ttggccgaat   3720
gagttcattg atgatgcatt gcttgattcg cgttccagaa ctaatgaatg ttaaagggat   3780
tggtagattt gaaagcatgt gtaggtcgag tataagagac ggattgattg aaaacaaggc   3840
atggctaacg tttttgagta gaattcaatc atatcgcatc ttagaactac caacttggac   3900
attgatttta tttgctctat catatgcttt ggttttgagt ccccgccttc actcctctcc   3960
ttcaactatg tcttcttatt tgcttgaggg caagcaaaga ctaagtttga gggagttgat   4020
atgtctataa tttgcatgtt ttcagtgtcc attcatcatc gttttgagtc cagtttcgta   4080
tcattcatca ctgttttata tcatttctca tcattcttgc atactttgca tgattaggat   4140
aactttgcat acatattgca tttctgagtt gttttcaggt gatttggagc tgtttgcaag   4200
caaattggaa gaaatgagcc agaaccagaa gacatactcg accctaggt cgagtgactt   4260 tggggccatt cttcccacat actcggcccc caggtcgagt gactttggag ccattcttcc   4320
catccactcg accaccgggt cgagtaacct tagctcaggc cactcgatga cactactcga   4380
ccccaggtcg agtatcactt cgccacacca cctgacaaca ctcgaccaat cactctacca   4440
agttactcga cccctggtc gagtatcatc actcaccacc atcagcatca ctcgaccgga   4500
cactcgatca cgtcttcaca gtctactcaa atccgcagtc aaccagacaa gctgagcaca   4560
```

-continued

```
aggaagagaa gaggagaaga caaagtgctt ggaagcggcc tggacctcca tcggatcacg    4620
aagcccatct cggcccatta tctctctatg ggccgagcga ttaggttatt ggcccgtcta    4680
ctatcatttt atttcgtttt gtataaatag atgtcttagg gttttgtcct gagacatcta    4740
gtcgacattg agttttttt gcttcagttt tattttctgt tctactctgc tgcgccgctt    4800
ttgcttctgc aacctgtaat tcgagatttt tccaagttat tcagattccg catttgattt    4860
```

<210> SEQ ID NO 10
<211> LENGTH: 648
<212> TYPE: PRT
<213> ORGANISM: Arabidopsis thaliana
<220> FEATURE:
<221> NAME/KEY: misc_feature
<222> LOCATION: (1)..(648)
<223> OTHER INFORMATION: Xaa = any amino acid

<400> SEQUENCE: 10

```
Met Ser Asn Tyr Ser Gly Glu Ser Ser Met Asp Ala Asp Tyr Asn Val
  1               5                  10                  15

Asp Glu Ala Glu Ser Trp Ser Thr Arg Pro Glu Arg Glu Gln Gln Ala
             20                  25                  30

Tyr Glu Ser Phe Arg Ala Glu Thr Gln Arg Ser Val Ala Arg Arg Asn
         35                  40                  45

Glu Arg Arg Ala Glu Ile Ala Arg Gly Lys Arg Ala Met Thr Ser Arg
     50                  55                  60

Tyr Glu Leu Ile Asp Glu Asp Ile Asp Val Glu Tyr Glu Pro Glu Ser
 65                  70                  75                  80

Trp His Arg Glu Thr Lys Leu Leu Asn Lys Pro Asp Glu Val Thr Val
                 85                  90                  95

Glu Glu Tyr Ile Arg Leu Phe Glu Leu Asn Asp Phe Trp Gly Ala Arg
            100                 105                 110

Tyr Pro Cys Tyr Glu Thr Leu Ala Gln Leu Arg Leu Leu Glu Asp Val
        115                 120                 125

Gln His Leu Phe Glu Lys Cys His Leu Glu Thr Leu Met Ser Tyr Pro
    130                 135                 140

Tyr Val Ala Tyr Lys Lys Glu Thr Ile Glu Phe Leu Ser Thr Leu Gln
145                 150                 155                 160

Val Glu Leu Tyr Gln Gly Leu Thr Ala Asp Glu Leu Glu Ser Glu Gly
                165                 170                 175

Leu Gly Phe Leu Thr Phe Ser Val Asn Glu Gln Arg Tyr Gln Leu Ser
            180                 185                 190

Ile Lys Ser Leu Glu Gly Leu Phe Gly Phe Pro Ser Gly Lys Gly Thr
        195                 200                 205

Lys Pro Lys Phe Glu Arg Glu Glu Leu Lys Asp Leu Trp Leu Thr Ile
    210                 215                 220

Gly Asn Asp Leu Ala Leu Asn Ser Ala Arg Ser Lys Ser Asn Gln Ile
225                 230                 235                 240

Arg Ser Pro Val Ile Arg Tyr Tyr Gln Arg Ser Val Ala Asn Val Leu
                245                 250                 255

Tyr Pro Arg Glu Ser Thr Gly Thr Val Ser Asn Thr Asp Met Glu Met
            260                 265                 270

Ile Asp Ser Ala Leu Lys Gly Ile Leu Arg Arg Thr Lys Gly Lys Lys
        275                 280                 285

Val Leu Lys Gly Asp Leu Asn Asp Thr Pro Pro Val Met Leu Leu Leu
    290                 295                 300
```

```
Ile His Met Cys Gly Tyr Arg Lys Trp Ala His Thr Asn Gly Arg Lys
305                 310                 315                 320

Lys Val Arg Gly Ala Leu Cys Val Gly Gly Val Thr Pro Ile Leu
            325                 330                 335

Ile Ala Cys Gly Val Pro Leu Thr Ser Pro Gly Phe Asp Pro Arg Met
                340                 345                 350

Met Asp Leu Asp His Leu Arg Arg Cys Glu Phe Leu Glu Tyr Asp Met
            355                 360                 365

Val Gly Asp Phe Tyr Arg Tyr Lys Phe Glu His Ser Leu Thr Arg Thr
        370                 375                 380

Ala Asn Ile Leu Leu Pro Cys Ile Glu Ala Thr Thr Ile Leu Xaa Gly
385                 390                 395                 400

Glu Asn Ile Asp Phe Arg Pro Ala Arg Asp Tyr Leu Tyr Phe Glu Ser
                405                 410                 415

Thr Pro Pro Thr Asp Asp Asn Val Pro Thr Thr Glu Ala Thr Glu Asp
                420                 425                 430

Asp Phe Ala Glu Thr Asp Glu Asp Arg Glu Glu Tyr Asp Thr Ser
            435                 440                 445

Met Tyr His Phe Ser Glu His Val Pro Pro Ala Gln Glu Ser Lys Ser
        450                 455                 460

Leu Ser Glu Ala His Arg Asn Asn Ser Lys Leu Gln Arg Trp Cys Lys
465                 470                 475                 480

Lys Gln Asp Arg Leu Leu Ile Lys Cys Phe Lys Ala Ile Thr Phe Leu
                485                 490                 495

Thr Asp Lys Ile Ser Cys Phe Ser Thr Thr Ala Ile Pro Gln Gly
                500                 505                 510

Glu Arg Pro Gln Asp Met Pro Ser Lys Arg Tyr Asp Ala Pro Gly Pro
            515                 520                 525

Ser His His Arg Pro Glu Pro Ser His His Arg Pro Glu Pro Ser Asp
530                 535                 540

Arg Val Val Pro Pro Val Pro Ala Arg His Ser Ser Phe Glu Pro Arg
545                 550                 555                 560

Glu Leu Gly Arg Lys Lys Ala Ala Leu Ala Arg Ser Gly Ser Arg
            565                 570                 575

Ser Arg Arg Leu Leu Gln Ser Arg Ser Leu Arg Asp Arg Gly Ala Gly
            580                 585                 590

Arg Ser Arg Arg Arg Glu Val Glu Tyr His Gln Ser Gly Ala Gly Arg
        595                 600                 605

Gly Glu Gly Ala Glu Val Glu Tyr Pro Gln Gly Glu Ala Glu Thr Gln
        610                 615                 620

Gln Gly Asp Ser Ser Met Ala Trp Glu Gln Ser Gln Ala Ala Ile Asp
625                 630                 635                 640

Asp Gln Leu Arg Ser Phe Phe His
            645

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 11
tggttcacca gataagctca gtgccctc                                    28
```

```
<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 12
cttcagactg gataggacta ggtgggcg                                28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 13
cgcccaccta gtcctatcca gtctgaag                                28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 14
cgcatcaaac aactaacaac gagggcac                                28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 15
cgataacatc gaccgtattg ctcgcc                                  26

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 16
aactagctcc catccgtctt cgacatcc                                28

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 17
tgcatcacac cggattggat tgac                                    24
```

```
<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 18
tgttcccctg aaccatagca atgagacc                                              28

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 19
caaacagaca gagtgtggcc caccacc                                               27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 20
caaacagaca gagtgtggcc caccacc                                               27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 21
tgcaaaccca caggaccaag tctaccc                                               27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide sequence

<400> SEQUENCE: 22
acagatggtg atagcgtgag cggtggc                                               27

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 23
tcaacctttt gccccaacaa ccactc                                                26

<210> SEQ ID NO 24
```

-continued

```
<211> LENGTH: 27
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 24
tctccatcca cgctttcctg aatgtcc                                      27

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 25
ggagaaggaa gctgaaaatc atattgtgg                                    29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 26
atgatgatcc taagtctacc cttttgcac                                    29

<210> SEQ ID NO 27
<211> LENGTH: 3122
<212> TYPE: DNA
<213> ORGANISM: Arabidopsis thaliana

<400> SEQUENCE: 27
ttcatatatt cgacctcttc ttctcattct tgcatccaaa agacacaaca agccgccatc    60
gctttccctc acaactctca ctcgaccacc gcccgctctc tcacttactc ggcttcatcg   120
ctctcatcgc catctctcaa catactcgac ctcgcgatat cactcgagct cgccgcttct   180
caccgcctct ccatcgtcac cgcctgctcc ctctctccaa ggaaacaact cgagctctcc   240
atttcactca ctcgacctct accaccaagc cggcttcacc acttctagct cttaaccact   300
cgaccacctt taccatcaac caatcaaatc gttttctcct ccattaaagc ttgacatact   360
cgaccgctga acacttatca ccttcaagct cctcatctct tcatcgtttc caacaccgct   420
gctctcatcc cccacgaaag cttgtcatca cctctcactc atcaccagtt cactcgattc   480
agcaaccaaa ctcgacctcg tctctcttgc cactcatagt cactcgatct ctcctcacca   540
tcttcatcat ctcccttact cgaccaccgt gcgtctcgct ccaccattgc catttaaaag   600
ctcactcgat tgtcaaagag aagaagagtg aagctcaacc accgccactc gaccgcgttt   660
ccctctacac attcaacact cgaccacggt gctaccatct ccacccgc tcttgttcac     720 catacactcg accaacaact ctcaaagtaa aaaaaaaaag aaaaaaaaag tcaaaaccga   780
cagtttcact caaccggttt actcgaccgg tacgctggtt tagattgtgt ttttggtttt   840
gctattacta acatattaac gtttatcttt gagtttcgtc tgttttttagg tttcatcatg   900 agtaactaca gtggaaaatc ctctatggac cctgattata atgtggatga agctaagtcc   960
tggtccacta gaccggagtg agagcaacat gtttacgaga gctataggga tgaatttgaa  1020
```

```
cgctctgcag ctcgacgtaa tcaaagaaga gctgaaatcg ctagaggaaa gagggcgatg    1080
tcgagtagat atgagctgat tgatgaggat atcaaaactg agtatgagcc agagtcatgg    1140
cgcaaggaga cgaagctact gaacaaatcc gacgaggtta cagtggagga gtatatcaga    1200
ttctttgaga tgaatgactt ctggggaacg aggtatccct gatatgagac tttagcccag    1260
ttggggttac tggaggacgt gcagcatctg ttcgagaagt gtcatctgat aaggaggaga    1320
caatcgagtt tctttccaca ctgcaagtgg aaatgtatga gggactcaca gactttgagc    1380
tggataccat ggggttaggc ttcttgacgt tcttagtgga tgaacagcgg taccagattt    1440
agatcaagaa attggaagaa ctgtttggtt tccctagtgg aaagggaacc aaccccaggt    1500
ttgacaggga gagcttaag gatttgtggg ctactattgg gaacaatcta ccgctaaact    1560
cgacgcggtc aagagcaac caaatccgga gtcctgtgat tcgctacttt cagcgctcgg    1620
ttgccaatgt ttttactcc agggagtcta caggcaccgt gtctaacaca gacatgaaga    1680
tgatagattc agcgcttata gggattctcc gccttacaaa aggaaagaat gtcctgagag    1740
gagatcttaa cgactcacca ccagtaatgc ctctgttgat ccatctgtgt gggtacatga    1800
agtgggcgct gacaaacggc aagaagaagg taagaggagc actatgcgtg ggtggcgttg    1860
tgacgccaat tctgaaagtt tgtggagttc cgctcaagga gtagggtta gcaccgagaa    1920 tgatggactt ggatcacttg cgccgatgtg agttctctga gtttgacatg gttggcgact    1980 tcaccgcta caggttcgag cattcatcga ttagaatcgc caacattctt ttccctgca    2040 tttacgctac taggattctc gagggcagga acattgactt caagcctgcg cttgaagatc    2100
tttatttcga gggcagtccg ccaactgagg agattagtca caccgaagga gctacaatag    2160
aagatgttga tgagacatat gatatagatg aggcggagtt tgacacgagc atgtatcatt    2220
tcagtgagca tatacctcca gcgaggaaaa gcaagagttt gagcgaagct cacaggaaca    2280
acagcaagct gcagaagtgg tgcaagaaac aggataagtt actcgccaag tgcctcaggg    2340
ctatcaagtt tctgaaggac aagatcagct gctcctcttc cactacaact attccgcaat    2400
gacagctccc tcaggacatg ccttcgagga gatatgacgc gcccgagcct agagagcaga    2460
agattctgca tgtccctgcg aggcattcat cattcgagcc tcgtgaatct aggaagaata    2520
ggagaacgac actcactcga tctagcagca ggagcagacg acttctgcag tctcgtagtt    2580
tacgcgaccg cggtgctggc cgcaatagaa gaagagaggt cgagtatcct cagagcggtg    2640
ctggccgcca cagagctgat gagatcgagt acccacatgc tggagctgat acggaacatg    2700
gcggttcgtc tatggcttgg gagcaatcac aggcagccat tgactaccaa cttcgttcat    2760
tattcgactg aggtaagcgc ctcacttcac cattatatta tatcatctct tgtgatttgt    2820 tcttttatttt gtttcagtga ttggatttgt cctgagtact ctcttccaag tttattcaca    2880
cagtggactg tgtgatttaa gtttggggga gggctcagga agtatgttgc attgtatata    2940 ttttttaagtc tgcattcatc taaggcatag aaaaaccaaa aaaaaattaa aaatttcaga    3000
aaatgatttc acaaaaaaag agtgttcatg tagttgcatt acatttagga tcaagtctag    3060
agtgtttcat ttaggattgt tgcatatgca taggggataa tgatgagata gccttgtaag    3120
ca                                                                   3122
```